(12) United States Patent
Franczyk, II

(10) Patent No.: US 6,274,760 B1
(45) Date of Patent: Aug. 14, 2001

(54) PREPARATION OF FORMYLPHOSPHONIC ACID FROM TERTIARY AMINOMETHYLPHOSPHONIC ACID N-OXIDES

(75) Inventor: Thaddeus S. Franczyk, II, Chesterfield, MO (US)

(73) Assignee: Monsanto Co., St. Louis, MO (US)

( * ) Notice: Subject to any disclaimer, the term of this patent is extended or adjusted under 35 U.S.C. 154(b) by 0 days.

(21) Appl. No.: 09/525,534

(22) Filed: Mar. 14, 2000

(51) Int. Cl.$^7$ ................................. C07F 9/38; C07F 9/40
(52) U.S. Cl. ................................. 562/17; 562/8; 562/24; 558/166; 558/169
(58) Field of Search .................... 562/17, 24, 8; 558/166, 169

(56) References Cited

U.S. PATENT DOCUMENTS

| | | | |
|---|---|---|---|
| 3,784,590 | 1/1974 | Firestone | 260/944 |
| 3,907,652 | 9/1975 | Wagenknecht et al. | 204/79 |
| 3,969,398 | 7/1976 | Hershman | 260/502.5 |
| 4,072,706 | 2/1978 | Hershman et al. | 260/502.5 |
| 4,264,776 | 4/1981 | Hershman et al. | 564/384 |
| 4,348,332 | 9/1982 | Oediger et al. | 260/502.4 R |
| 4,568,432 * | 2/1986 | Rogers . | |
| 4,624,937 | 11/1986 | Chou | 502/180 |
| 4,937,376 | 6/1990 | Fields, Jr. et al. | 562/16 |
| 5,023,369 | 6/1991 | Fields, Jr. | 562/17 |
| 5,043,475 | 8/1991 | Fields, Jr. | 562/17 |
| 5,047,579 | 9/1991 | Glowka et al. | 562/17 |
| 5,072,033 | 12/1991 | Fields, Jr. et al. | 562/17 |

FOREIGN PATENT DOCUMENTS

98/50391 * 11/1998 (WO) .

OTHER PUBLICATIONS

CA:116:173339 abs J Chem Soc Perkin Trans 2 by Croft (2) pp 153–60, 1992.*

CA:97169801 abs of Vestn. Mosk. univ. Ser 2: Kim. 23 (4) p. 378–82, 1982*

Cairns, J., et al. "The Synthesis and Chemistry of Formylphophonate," *Phosphorus, Sulfur, and Silicon* vols. 144–146 (1999), pp. 385–388.

Hamilton, R., M.A. McKervey, M.D. Rafferty, & B.J. Walker. "Reactions of Diazomethylphosphonate: The First Synthesis of a Formylphosphonyl Hydrate," *Phosphorus, Sulfur, and Silicon* vols. 109–110 (1996), pp. 441–444.

Hamilton, R., M.A. McKervey, M.D. Rafferty, & B.J. Walker, *J. Chem. Soc.–Chem. Commun.* (1994), p. 37.

Riley, Dennis P., & Donald L. Fields, "Electron–Transfer Agents in Metal–Catalyzed Dioxygen Oxidation: Effective Catalysts for the Interception and Oxidation of Carbon Radicals," *J. Am. Chem. Soc. 114* (Feb. 26, 1992), pp. 1881–1882.

Riley, Dennis P., Donald L. Fields, & W. Rivers. *J. Am. Chem. Soc. 113*(1991), p. 3371.

Riley, Dennis P., Donald L. Fields, & W. Rivers. *Inorg. Chem. 30*(1991), p. 4191.

(List continued on next page.)

Primary Examiner—Jean F. Vollano
(74) Attorney, Agent, or Firm—Ira D. Finkelstein; Howrey Simon Arnold & White, LLP

(57) ABSTRACT

Formylphosphonic acid derivatives are prepared by the catalytic decomposition of a (phosphonomethyl)amine N-oxide compound to form the formylphosphonic acid derivative and a dephosphonomethylated amine.

120 Claims, 4 Drawing Sheets

OTHER PUBLICATIONS

Riley, Dennis P., & Paul E. Correa, "An Unprecedented Selective Autoxidation of Tertiary Amines to Amine Oxides", *J. Org. Chem. 50*(1985), pp. 1563–1564.

Beckwith, Athelstan L.J., et al., "Amine Autoxidation in Aquesous Solution", *Aust. J. Chem. 36*(1983), pp. 719–739.

Vasella, Andrea, & Robert Voeffray, "Asymmetric Synthesis of α–aminophosphonic Acids by Cycloaddition of N–glycosyl–C–dialkyloxphosphonoylnitrones", *Helv. Chim. Acta 65*, 7 (1982), pp. 1953–1964.

Wagenknecht, J.H., F.S. Stover, W.G. Wagner, & R.S. Mitchell, *Syn. React. Inorg. Metal–Org. Chem. 12*(1982), pp. 1–9.

Stover, F.S., & J.H. Wagenknecht, *Analytica Chim. Acta 135*(1982), pp. 347–350.

Livantsov, M.V., et al., "Phosphorylation of Orthoformates," *Zh. Obsh. Khim.* vol. 52 No. 4 (1982), p. 930.

Gross, H., *Sitzungsber. Akad. Wiss. DDr*, 1979, Issue 14N, pp. 23–31.

Alt, G.H. & J.H. Wagenknecht, *Syn. React. Inorg. Metal–Org. Chem. 4* (1974), pp. 255–262.

Wagenknecht, John H, "Electrochemical Oxidation of N–Substituted Iminodimethylene–diphosphonic Acids", *J. Electrochem. Soc. 123*, 5 (May 1976), pp. 620–624.

Wagenknecht, John. *An Electrochemical Method for the Preparation of Iminodimethylene–diphosponic Acid, Syn. React. Inorg. Metal–Org. Chem., 4*, 6 (1974), pp. 567–572.

S.S. Krokhina et al., "Reaction of Triethylorthoformate on Some Trivalent Phosphorus Derivatives", *Izv. Akad. Nauk SSSR*, Ser. Khim., No. 6, p. 1420 (Jun. 1968).

\* cited by examiner

PREPARATION OF FORMYLPHOSPHONIC ACID FROM TERTIARY AMINOMETHYLPHOSPHONIC ACID N-OXIDES

BACKGROUND OF THE INVENTION

1. Field of the Invention

This invention relates to the preparation of formylphosphonic acid, its salts, and its esters, and particularly to novel processes for the preparation of formylphosphonic acid by the catalytic decomposition of a (phosphonomethyl)amine N-oxide compound in the presence of a decomposition catalyst.

2. Description of Related Art

Phosphorus-containing compounds such as formylphosphonic acid are important precursors for the synthesis of organophosphorus compounds. Such organophosphorus compounds have numerous applications. For example, formylphosphonic acid can be used as a precursor in the synthesis of N-(phosphonomethyl)glycine, a highly effective commercial herbicide (common name glyphosate, available under the trade name Roundup®) useful for the control of a large variety of weeds. Formylphosphonic acid can alternatively be used as an advanced intermediate in the preparation of medicinally important compounds such as the antiviral agent phosphono hydroxyacetic acid. As a reagent or intermediate, formylphosphonic acid has potential for chemical transformation at the carbonyl, phosphorus, or hydroxyl moieties.

Researchers have reported electrochemical processes in which formylphosphonic acid forms. For example, Wagenknecht (Synth. React. Inorg. Met.-Org. 4:567–572 (1974)) spectrophotometrically observes or isolates formylphosphonic acid in the electrochemical oxidation of nitrilotris (methylenephosphonic acid) to the secondary amine. A similar reaction is reported in U.S. Pat. No. 3,907,652. In J. Electrochem. Soc. 123:620–624 (1976) Wagenknecht reports the electrochemical oxidation of substituted iminodimethylenediphosphonic acids to produce the secondary amine. In that study, formylphosphonic acid was isolated in unreported yield as a side product. Wagenknecht, et al. again reports the formation of formylphosphonic acid as a side product in the electrochemical oxidation of nitrilotris (methylenephosphonic acid) in Synth. React. Inorg. Met.-Org. 12:1–9 (1982). However, these reactions suffer from several shortcomings. Yields of formylphosphonic acid are poor or unreported. Wagenknecht (1982) reports that formylphosphonic acid degrades under the electrolysis reaction conditions. The electrochemical reaction requires the addition of a strong hydrochloric acid solution which presents safety, environmental, and equipment corrosion problems. Electrochemical methods generally require an external power source and other equipment which typically have higher maintenance needs and costs than do non-electrochemical reactions. It would be advantageous to have a method for the preparation of formylphosphonic acid in high yield which does not require specialized electrochemical equipment and does not require the handling of large quantities of strong mineral acids.

Hershman et al., in U.S. Pat. No. 4,072,706, disclose a process in which (phosphonomethyl)amines are oxidized with molecular oxygen in the presence of an activated carbon catalyst to cleave a phosphonomethyl group and produce a secondary amine. According to Hershman et al., formylphosphonic is produced as an intermediate cleavage fragment, with the fragment undergoing hydrolysis in a second step to formic acid and phosphonic acid. Hershman et al., however, identify formylphosphonic acid as an intermediate cleavage fragment in only one reaction run and although the yield is unreported it is apparently low. In addition, Hershman et al. fail to disclose any means to limit the hydrolysis of the intermediate cleavage fragment.

Disclosures have been made of a process wherein N-(phosphonomethyl)iminodiacetic acid N-oxide is catalytically decarboxymethylated to form N-(phosphonomethyl)glycine, carbon dioxide, and formaldehyde. For example, Fields, et al. disclose such a reaction in U.S. Pat. No. 5,043,475. However, the Fields, et al. decarboxymethylation is highly selective for an acetic acid arm of the N-oxide and cleavage of the phosphonomethyl arm is not reported.

Thus, a need exists for a convenient, environmentally-compatible, safe, and cost-effective process for the reaction of aminomethylphosphonic acid derivatives to produce formylphosphonic acid in high yield with minimal degradation.

SUMMARY OF THE INVENTION

To address this and other needs, an improved process for the manufacture of formylphosphonic acid derivatives is now disclosed. Among the several objects of the present invention is an improved process for the manufacture of formylphosphonic acid, its esters, salts, acetals, hemiacetals, and hydrate.

Briefly, therefore, one aspect of the present invention is directed to a process for the preparation of formylphosphonic acid, its esters, salts, acetals, hemiacetals, and hydrate (collectively herein referred to as formylphosphonic acid derivatives), especially of formylphosphonic acid, wherein the process comprises decomposing a (phosphonomethyl) amine N-oxide compound in the presence of a decomposition catalyst to produce the formylphosphonic acid derivative and a dephosphonomethylated amine.

The present invention is also directed to a process for the preparation of formylphosphonic acid, its esters, salts, acetals, hemiacetals, and hydrate, especially of formylphosphonic acid, wherein the process comprises oxidizing nitrilotris(methylenephosphonic acid) or a salt thereof to form nitrilotris(methylenephosphonic acid) N-oxide or a salt thereof, and decomposing the nitrilotris (methylenephosphonic acid) N-oxide or salt thereof in the presence of a decomposition catalyst.

Another aspect of the present invention is directed to a process for preparing N-(phosphonomethyl)glycine, or a salt or an ester thereof, wherein the method comprises decomposing a (phosphonomethyl)amine N-oxide compound in the presence of a decomposition catalyst to produce a formylphosphonic acid derivative and a dephosphonomethylated amine, and reacting the formylphosphonic acid derivative to produce N-(phosphonomethyl)glycine or a salt or an ester thereof. Of particular interest is an embodiment of this process in which the reaction to produce N-(phosphonomethyl)glycine is achieved by condensing the formylphosphonic acid derivative with a glycine compound, and reducing the condensed product to produce N-(phosphonomethyl)glycine. Another embodiment which is of particular interest is one in which the formylphosphonic acid derivative is condensed with 1-amino-2-hydroxyethane to produce a condensed alcohol intermediate, the condensed alcohol intermediate is reduced to produce an N-(2-hydroxyethyl)-N-(phosphonomethyl)amine compound, and the N-(2-hydroxyethyl)-N-(phosphonomethyl)amine compound is oxidized to produce N-(phosphonomethyl)glycine.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will become apparent to those skilled in the art from this detailed description.

DESCRIPTION OF ILLUSTRATIVE EMBODIMENTS

Figure 1:
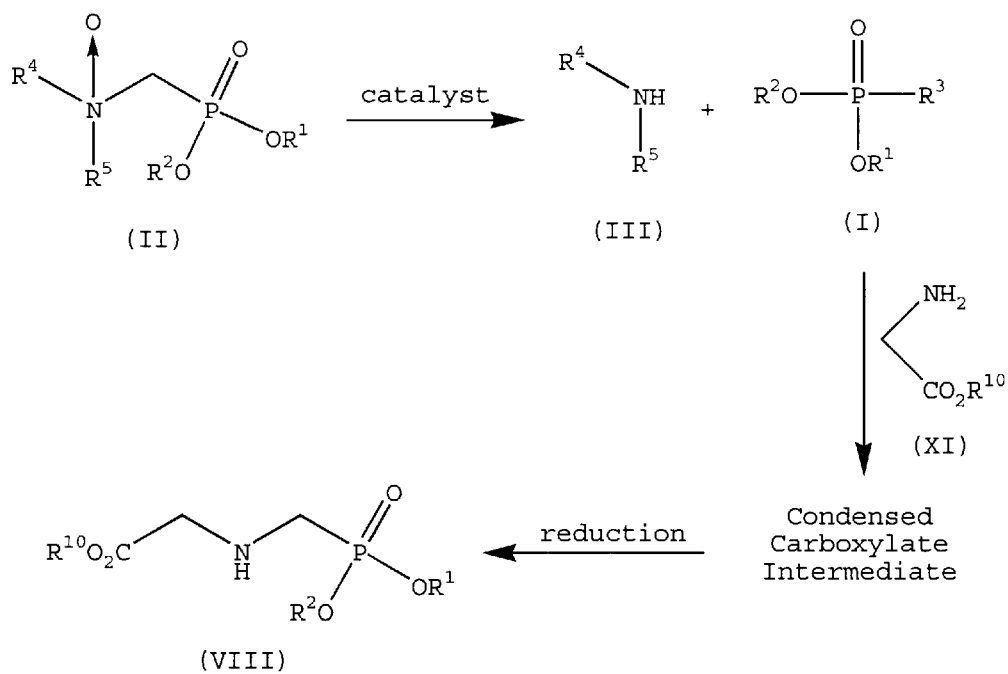
FIG. 1 is a general scheme for the decomposition of a (phosphonomethyl)amine oxide to form a formylphosphonic acid derivative and a dephosphonomethylated amine; the condensation of the formylphosphonic acid derivative with a glycine compound, or a salt, ester, or zwitterion thereof, to form a condensed carboxylate intermediate; and the reduction of the condensed carboxylate intermediate to produce N-(phosphonomethyl)glycine or a salt or an ester thereof.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

a. Definitions

The following definitions are provided in order to aid the reader in understanding the detailed description of the present invention:

"Hydrocarbyl" means a group composed of carbon and hydrogen. This definition includes alkyl, alkenyl, and alkynyl groups which are each straight chain, branched chain, or cyclic hydrocarbons from one to about twenty carbons. Also included in this definition are aryl groups composed of carbon and hydrogen. Hydrocarbyl therefore includes, for example, methyl, ethyl, propyl, butyl, pentyl, hexyl, cyclopropyl, cyclobutyl, cyclopentyl, cyclohexyl, methylcyclopentyl, ethenyl, propenyl, butenyl, pentenyl, hexenyl, ethynyl, propynyl, butynyl, pentynyl, hexynyl, phenyl, naphthyl, anthracenyl, benzyl, and isomers thereof.

"Substituted hydrocarbyl" means a hydrocarbyl group in which one or more hydrogen has been substituted with a heteroatom-containing group. Such substituent groups include, for example, halo, oxo, heterocycle, alkoxy, hydroxy, aryloxy, $-NO_2$, amino, alkylamino, or amido. When the substituent group is oxo, the substituted hydrocarbyl can be, for example, an acyl group.

"Heteroatom" means an atom of any element other than carbon or hydrogen which is capable of forming chemical bonds.

"Heterocycle" means a saturated or unsaturated mono- or multi-ring carbocycle wherein at least one carbon atom is replaced by N, S, P, or O. This includes, for example, the following structures:

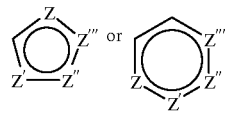

wherein Z, Z', Z", or Z''' is C, S, P, 0, or N, with the proviso that one of Z, Z', Z", or Z''' is other than carbon, but is not O or S when attached to another Z atom by a double bond or when attached to another O or S atom. Furthermore, the optional substituents are understood to be attached to Z, Z', Z", or Z''' only when each is C. The point of attachment to the molecule of interest can be at the heteroatom or elsewhere within the ring.

"Halogen" or "halo" means a fluoro, chloro, bromo, or iodo group.

"NMR" means nuclear magnetic resonance spectroscopy.

"Dephosphonomethylated amine" means a primary or secondary amine which has been produced by removing at least one phosphonomethyl group from a secondary or tertiary (phosphonomethyl)amine compound.

b. Process Details

In accordance with the present invention, it is now disclosed that a formylphosphonic acid derivative can surprisingly be obtained in high yield by decomposing a (phosphonomethyl)amine N-oxide compound in the presence of a decomposition catalyst to produce the formylphosphonic acid derivative and a dephosphonomethylated amine. In one aspect of the present invention, the formylphosphonic acid derivative has the structure of formula (I), the (phosphonomethyl)amine N-oxide has the structure of formula (II), and the dephosphonomethylated amine has the structure of formula (III), shown in eq. 1.

eq. 1

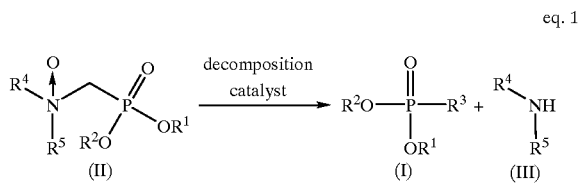

In eq. 1, $R^1$ and $R^2$ can independently be H, hydrocarbyl, substituted hydrocarbyl, heterocycle, or a salt-forming cation. Taken together with the oxygen and phosphorus atoms to which they are attached, $R^1$ and $R^2$ can optionally form a cyclic structure. Without meaning to limit the breadth of the current invention, examples of salt-forming cations include $Na^+$, $K^+$, $Li^+$, $Ca^{2+}$, $NH_4^+$, trialkylsulfonium cations, alkylammonium cations, dialkylammonium cations, trialkylammonium cations, and quaternary ammonium cations. $R^3$ can be —CHO or —CH(OR$^8$)(OR$^9$). $R^4$ and $R^5$ are independently selected from the group consisting of H, —CH$_2$PO(OR$^6$)(OR$^7$), hydrocarbyl, substituted hydrocarbyl, and heterocycle. Taken together with the nitrogen atom to which they are attached, $R^4$ and $R^5$ can optionally form a cyclic structure. $R^6$ and $R^7$ can independently be H, hydrocarbyl, substituted hydrocarbyl, heterocycle, or a salt-forming cation. Taken together with the oxygen and phosphorus atoms to which they are attached, $R^6$ and $R^7$ can optionally form a cyclic structure. $R^8$ and $R^9$ can independently be H, hydrocarbyl, substituted hydrocarbyl, or heterocycle. Taken together with the oxygen and carbon atoms to which they are attached, $R^8$ and $R^9$ can optionally form a cyclic structure.

The process of the present invention may be run in the presence of a solvent, preferably water or an organic solvent. Preferred organic solvents include alcohols. Non-limiting examples of alcohols useful as solvents include aliphatic alcohols, aromatic alcohols, glycols, polyols, and unsaturated alcohols.

When the process of the present invention is run in the presence of water, the formylphosphonic acid derivative product can comprise the hydrate or a mixture of the hydrate and the aldehyde. When the process is run in the presence of an alcohol, the formylphosphonic acid derivative product can comprise an acetal or a mixture of an acetal and the aldehyde. When the process is run in the presence of both water and an alcohol, the formylphosphonic acid derivative product can comprise an acetal, a hemiacetal, the hydrate, the aldehyde, or mixtures thereof. The hydrate is represented by formula (I) wherein $R^3$ is —CH(OR$^8$)(OR$^9$), and $R^8$ and $R^9$ are both H. The aldehyde is represented by formula (I) wherein $R^3$ is —CHO. An acetal is represented by formula (I) wherein $R^3$ is —CH(OR$^8$)(OR), and $R^8$ and $R^9$ are independently hydrocarbyl, substituted hydrocarbyl, or heteroaryl. In the case of an acetal, $R^8$ and $R^9$ taken together with the oxygen and carbon atoms to which they are attached can optionally form a cyclic structure. A hemiacetal is represented by formula (I) wherein $R^3$ is —CH(OR$^8$)(OR$^9$), one of $R^8$ and $R^9$ is H, and the other of $R^8$ and $R^9$ is hydrocarbyl, substituted hydrocarbyl, or heteroaryl.

The decomposition catalyst used in the present invention can vary widely in its physical and chemical nature. In one aspect of the present invention, the decomposition catalyst comprises a metal. Preferably, the metal is iron, zinc, aluminum, vanadium, molybdenum, or copper. The metal is useful as a decomposition catalyst in a variety of valence states. For example, the metal can be present in a zero valence state or in a charged valence state. When in a zero valence state, the metal can be in a metallic form. In a preferred embodiment the metal is in a salt or an oxide form. More preferably, the decomposition catalyst comprises a vanadium salt, an iron salt, or a copper salt. Suitable decomposition catalysts that can be used in the present process include vanadium pentoxide, vanadyl sulfate, vanadium chloride, ferrous sulfate, ferrous chloride, ferrous bromide, and the like. Still more preferably, the decomposition catalyst comprises a vanadium salt. In an especially preferred embodiment, the decomposition catalyst comprises vanadyl sulfate (VOSO$_4$).

The decomposition catalyst can be homogeneous or heterogeneous. When the decomposition catalyst is heterogeneous, it can be present, for example, in a metallic form such as copper metal, iron filings, zinc filings, or aluminum metal. When the decomposition catalyst is homogeneous, it is preferably in the form of a water-soluble compound or a compound which is soluble in the reaction mixture.

Surprisingly, a wide range of reaction conditions can be used when practicing the instant invention. Typically the temperature at which the inventive process is run can vary over the range of about 0° C. to about 150° C., preferably about 20° C. to about 110° C., more preferably about 20° C. to about 75° C.

A wide variety of reaction times can be used in the process of the present invention. Typically the decomposition reaction is very rapid, having achieved a high rate of conversion of starting material in a short period of time, e.g. minutes. However, the general stability of the formylphosphonic acid derivative in the product mixture allows longer reaction times to be used, if desired.

The initial concentration of the (phosphonomethyl)amine N-oxide compound can vary widely in the process of the present invention. The process can be run at any convenient initial concentration of the (phosphonomethyl)amine N-oxide compound. Preferably, the initial concentration of the (phosphonomethyl)amine N-oxide compound is less than about 65 wt %, more preferably less than about 50 wt %, still more preferably less than about 35 wt %, and more preferably still less than about 10 wt %.

The process of the present invention can be carried out under a wide variety of acidic, basic, or neutral conditions. Preferably at least part of the course of the decomposition reaction is carried out at neutral or acidic conditions, more preferably at about pH 3 or less. Still more preferably, the entire course of the decomposition reaction is carried out at about pH 3 or less.

In one embodiment, at least one of $R^4$ and $R^5$ of eq. 1 is —CH$_2$PO(OR$^6$)(OR$^7$). In another embodiment, $R^4$ and $R^5$ are independently hydrocarbyl or —CH$_2$PO(OR$^6$)(OR$^7$). In a preferred embodiment, both $R^4$ and $R^5$ are —CH$_2$PO(OR$^6$)(OR$^7$). When both $R^4$ and $R^5$ are —CH$_2$PO(OR$^6$)(OR$^7$), it is especially preferred that $R^6$ and $R^7$ are independently H or a salt-forming cation. This especially preferred embodiment is illustrated in eq. 2, wherein $R^1$, $R^2$, and $R^3$ are as defined for eq. 1.

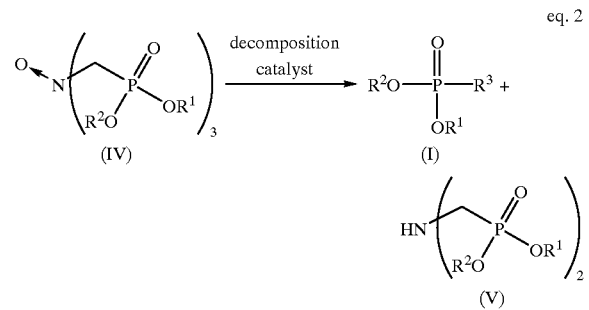

eq. 2

In another embodiment, $R^4$ and $R^5$ of eq. 1 are both hydrocarbyl. Alternatively, one of $R^4$ and $R^5$ of eq. 1 can be hydrocarbyl while the other of $R^4$ and $R^5$ is —CH$_2$PO(OR$^6$)(OR$^7$).

In yet another embodiment of the present invention, one of $R^4$ and $R^5$ of eq. 1 is —CH$_2$PO(OR$^6$)(OR$^7$) and the other of $R^4$ and $R^5$ is —CH$_2$CH$_2$OH. In this embodiment, the products of the decomposition reaction comprise a formylphosphonic acid derivative and N-(2-hydroxyethyl)-

N-(phosphonomethyl)amine, or salts or zwitterions thereof. The formylphosphonic acid derivative can be used for a variety of purposes as described herein, including the production of N-(phosphonomethyl)glycine. The N-(2-hydroxyethyl)-N-(phosphonomethyl)amine or its salts or zwitterions can be used to directly produce N-(phosphonomethyl)glycine via oxidation as described hereinbelow.

It is a further object of the present invention to provide a process wherein the dephosphonomethylated amine (formula (III)) produced in the decomposition of the (phosphonomethyl)amine N-oxide is reacted under phosphonomethylation conditions to produce a (phosphonomethyl)amine compound which is oxidized to regenerate the (phosphonomethyl)amine N-oxide compound (formula (II)). An advantage of this process is to recycle the dephosphonomethylated amine, thereby avoiding environmental and economic waste. Eq. 3 shows this dephosphonomethylated amine recycle process. Phosphonomethylation reaction conditions useful in the present invention are well known to those of skill in the art and examples can be found in, e.g., *Glyphosate: A Unique Global Herbicide*, ACS Monograph 189, J. E. Franz, et al., American Chemical Society, Washington D.C., 1997, pp. 236–245, herein incorporated by reference.

eq. 3

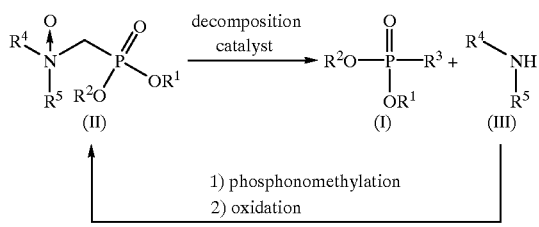

For example, the phosphonomethylation reaction conditions can comprise reacting the dephosphonomethylated amine in the presence of phosphorus trichloride, water, and a source of formaldehyde to produce the (phosphonomethyl)amine compound. Alternatively, the phosphonomethylation reaction conditions can comprise reacting the dephosphonomethylated amine in the presence of phosphorous acid, a strong acid, and a source of formaldehyde to produce the (phosphonomethyl)amine compound.

The process of the present invention can be operated in a continuous mode wherein the (phosphonomethyl)amine N-oxide compound is continuously or intermittently introduced to a continuous reaction zone and from which a reaction product mixture comprising the formylphosphonic acid derivative is continuously or intermittently withdrawn. An example of a continuous reaction zone useful in the inventive process is a tube reactor packed with a heterogeneous decomposition catalyst. Other examples of continuous reaction zones useful for the inventive process include a continuous stirred tank reactor or a cascade of stirred tanks.

The (phosphonomethyl)amine N-oxide useful in the present invention can be prepared by many different methods. For example, Fields, et al. (U.S. Pat. No. 5,043,475, herein incorporated by reference) disclose methods for the preparation of N-(phosphonomethyl)iminodiacetic acid N-oxide by treatment of N-(phosphonomethyl) iminodiacetic acid with a peroxide in the presence of an oxidation catalyst. (Phosphonomethyl)amine N-oxides useful in the present invention can be prepared by similar methods. For example, a (phosphonomethyl)amine (formula (VI)) can be treated with an oxidizing agent in the presence of an oxidation catalyst to form the (phosphonomethyl)amine N-oxide. Oxidizing agents useful in the present invention include without limitation peroxides such as hydrogen peroxide, performic acid, peracetic acid, perbenzoic acid, peroxytrifluoroacetic acid, benzoyl peroxide, benzenepersulfonic acid, and combinations thereof. Hydrogen peroxide is a particularly preferred oxidizing agent. Oxidation catalysts useful in the present process include metals and metal complexes. Especially useful oxidation catalysts include transition metals and transition metal complexes. Examples of useful transition metal oxidation catalysts include molybdenum, tungsten, cobalt, silver, iron, nickel, chromium, ruthenium, vanadium, cerium, manganese, and complexes and salts thereof. Other metals which are useful as oxidation catalysts in the present invention include aluminum, tin, lead, and complexes and salts thereof. Suitable salts include manganese acetate, manganese sulfate, manganese (II or III) acetylacetonate, cobalt sulfate, cobalt (II or III) acetylacetonate, cobalt chloride, cobalt bromide, cobalt nitrate, cobalt acetate, ceric ammonium sulfate, ceric ammonium nitrate, ferric ammonium sulfate, nickel bromide, chromium chloride, ruthenium chloride, ruthenium bromide, aluminum nitrate, vanadyl sulfate, vanadium bromide, vanadium chloride, tungstic acid, 1,2-tungstophosphate, barium tungstate, sodium tungstate, potassium tungstate, and the like. It is preferred to use manganese, cobalt, vanadiun, tungsten, cerium, or salts or complexes thereof. Especially preferred are cobalt, tungsten, vanadium, or salts or complexes thereof. A particularly preferred oxidation catalyst is sodium tungstate ($Na_2WO_4$). Additional oxidation catalysts useful for the preparation of (phosphonomethyl)amine N-oxide compounds are disclosed in Fields, et al., U.S. Pat. No. 4,937,376, herein incorporated by reference.

The oxidation of a (phosphonomethyl)amine compound with a peroxide to form a (phosphonomethyl)amine N-oxide compound can be aided by adding a catalytic amount of a metabisulfite compound in the presence of a molybdenum oxidation catalyst. Glowka, et al. disclose in U.S. Pat. No. 5,047,579 (herein incorporated by reference) a process wherein the yield of N-(phosphonomethyl)iminodiacetic acid N-oxide from the oxidation of N-(phosphonomethyl) iminodiacetic acid in the presence of a water-soluble molybdenum oxidation catalyst is increased by the presence of a metabisulfite compound. Metabisulfite compounds useful in the present invention include, for example, sodium metabisulfite.

According to the present invention, therefore, a (phosphonomethyl)amine compound, for example nitrilotris (methylenephosphonic acid), can be oxidized according to methods known to those of skill in the art to a (phosphonomethyl)amine N-oxide compound, for example nitrilotris(methylenephosphonic acid) N-oxide. The (phosphonomethyl)amine N-oxide compound can be catalytically decomposed according to conditions disclosed herein to form a formylphosphonic acid derivative and a dephosphonomethylated amine. This novel sequence is generically shown in eq. 4.

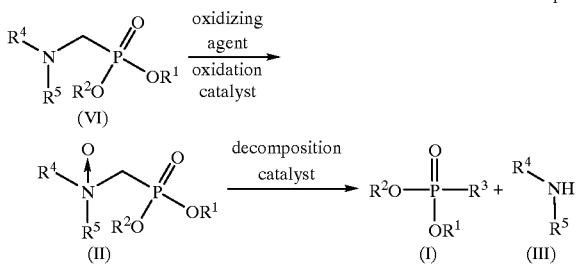

eq. 4

It is contemplated that the process of the present invention for the production of formylphosphonic acid derivatives from (phosphonomethyl)amine compounds can be carried out in sequential steps, for example, in a series of vessels. Alternatively, the process of the present invention can be carried out in a single step, for example in a single vessel. For example, formylphosphonic acid can be produced in a single step by adding an oxidizing agent to a (phosphonomethyl)amine compound in the presence of one or more catalysts effective for the oxidation of the (phosphonomethyl)amine compound (VI) and for the decomposition of the (phosphonomethyl)amine N-oxide compound (II) to the formylphosphonic acid derivative (I). Oxidation catalysts useful as decomposition catalysts include vanadium metal, vanadium salts, and vanadium oxides, such as vanadyl sulfate. Alternatively, a mixture of oxidation catalysts and decomposition catalysts can successfully be used in the current embodiment. In another alternative, oxidation catalysts and decomposition catalysts can be added to the single reaction mixture in a sequential fashion.

Alternatively, the intermediate (phosphonomethyl)amine N-oxide compound can be isolated or stored in either isolated or unisolated form for a period of time prior to a decomposition step to form the formylphosphonic acid derivative. Generally, oxidizing agents such as the peroxides discussed in this disclosure are useful for either the single-step or for the sequentially-stepped production of formylphosphonic acid derivatives from (phosphonomethyl) amine N-oxide compounds. The (phosphonomethyl)amine compounds useful in the present invention include those represented by formula (VI) in eq. 4. In a particularly preferred embodiment of the present invention, the oxidation catalyst for the conversion of the (phosphonomethyl) amine compound to the (phosphonomethyl)amine N-oxide compound comprises or serves as the source of the decomposition catalyst.

It is another object of the present invention to provide a process for the preparation of N-(phosphonomethyl)glycine, or a salt or an ester thereof wherein the process comprises reacting a (phosphonomethyl)amine N-oxide compound in the presence of a decomposition catalyst to produce a formylphosphonic acid derivative and a dephosphonomethylated amine, and further reacting the formylphosphonic acid derivative to produce N-(phosphonomethyl)glycine, or a salt or an ester thereof. The reaction of the formylphosphonic acid derivative to produce N-(phosphonomethyl) glycine and its salts and esters can be achieved by a number of different methods. For example, the reaction can be achieved by contacting the formylphosphonic acid derivative with a glycine compound (formula XI) to form a condensed carboxylate intermediate, and reducing the condensed carboxylate intermediate to produce N-(phosphonomethyl)glycine, or a salt or an ester thereof (formula (VIII)). Examples of procedures by which a formylphosphonic acid derivative is condensed with a glycine compound and reduced to produce N-(phosphonomethyl)glycine are disclosed in U.S. Pat. No. 4,568,432, herein incorporated by reference. An example of a way in which the reduction of the condensation product of the formylphosphonic acid derivative with the glycine compound can be achieved is by hydrogenation. For example, the condensation product can be hydrogenated in the presence of hydrogen and a hydrogenation catalyst such as a noble metal. Examples of noble metals useful as hydrogenation catalysts include platinum, palladium, nickel, and copper. If desired, the catalyst can have a very high surface area, such as Raney nickel. Alternatively, the hydrogenation catalyst can further comprise a solid support such as carbon. For example, the hydrogenation catalyst can comprise a noble metal on carbon. A hydrogenation catalyst useful in the present invention is palladium on carbon.

The process whereby the (phosphonomethyl)amine N-oxide compound is reacted with a glycine compound to produce a condensed carboxylate intermediate and then reduced to produce N-(phosphonomethyl)glycine or a salt or an ester thereof is presented generically in FIG. 1. $R^1$, $R^2$, $R^3$, $R^4$, and $R^5$ in FIG. 1 each has the meaning defined previously in this disclosure. $R^{10}$ can be H, hydrocarbyl, substituted hydrocarbyl, heteroaryl, or a salt-forming cation.

The reaction of formylphosphonic acid to produce N-(phosphonomethyl)glycine or its salts or its esters can also be achieved by condensing the formylphosphonic acid derivative with 1-amino-2-hydroxyethane to form a condensed alcohol intermediate; reducing the condensed alcohol intermediate to produce an N-(2-hydroxyethyl)-N-(phosphonomethyl)amine compound, or a salt or an ester thereof (formula (IX)); and oxidizing the N-(2-hydroxyethyl)-N-(phosphonomethyl)amine compound to produce N-(phosphonomethyl)glycine, or a salt or an ester thereof (formula (VIII)). The condensation of a formylphosphonic acid derivative with 1-amino-2-hydroxyethane to produce a condensed alcohol intermediate can be performed in a procedure similar to that disclosed in U.S. Pat. No. 4,568,432, herein incorporated by reference, for the condensation of glycine with formylphosphonic acid. The reduction of the condensed alcohol intermediate, thereby producing N-(2-hydroxyethyl)-N-(phosphonomethyl)amine, can be performed in a manner similar to that disclosed in U.S. Pat. No. 4,568,432 for the reduction of the condensation product of glycine with formylphosphonic acid.

An example of a way in which the reduction of the condensed alcohol intermediate can be achieved is by hydrogenation. For example, the condensation product can be hydrogenated in the presence of hydrogen and a hydrogenation catalyst such as a noble metal. Examples of noble metals useful as hydrogenation catalysts include platinum, palladium, nickel, and copper. If desired, the catalyst can have a very high surface area, such as Raney nickel. Alternatively, the hydrogenation catalyst can be a supported catalyst such as noble metal on carbon. A useful supported catalyst is palladium on carbon.

The oxidation of the N-(2-hydroxyethyl)-N-(phosphonomethyl)amine compound to produce N-(phosphonomethyl)glycine, or a salt or an ester thereof can be achieved by a number of different methods. For example, the oxidation of the N-(2-hydroxyethyl)-N-(phosphonomethyl)amine compound can be achieved by dehydrogenated. A useful method for the oxidation via dehydrogenation of N-(2-hydroxyethyl)-N-(phosphonomethyl)amine to produce N-(phosphonomethyl)

glycine is disclosed by Ebner, et al., in U.S. Pat. No. 5,627,125, herein incorporated by reference.

Figure 2:
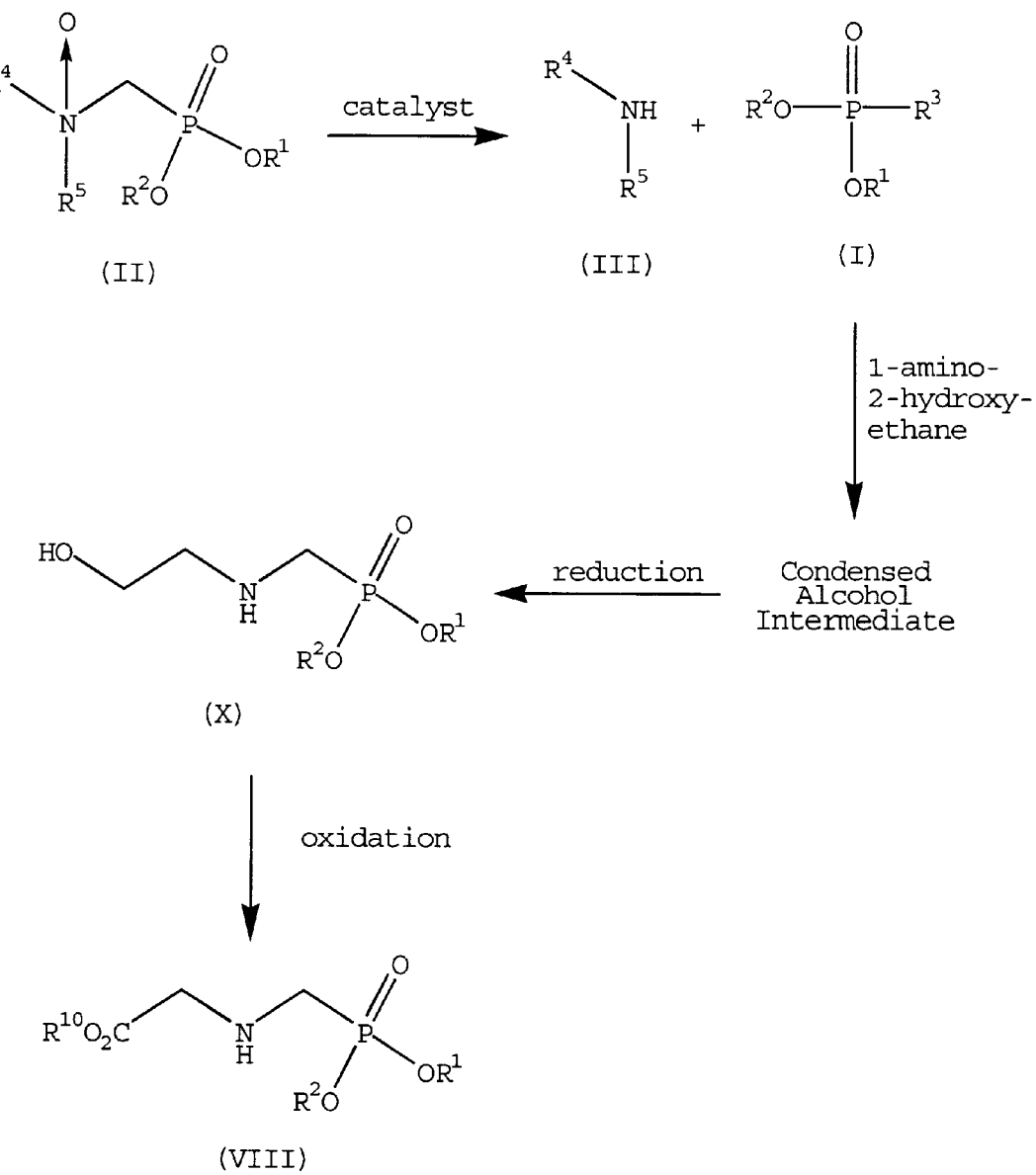
FIG. 2 is a general synthetic scheme for the decomposition of a (phosphonomethyl)amine oxide to form a formylphosphonic acid derivative and a dephosphonomethylated amine; the condensation of the formylphosphonic acid derivative with 1-amino-2-hydroxyethane to form a condensed alcohol intermediate; the reduction of the condensed alcohol intermediate to produce N-(2-hydroxyethyl)-N-(phosphonomethyl)amine; and the oxidation of N-(2-hydroxyethyl)-N-(phosphonomethyl)amine to form N-(phosphonomethyl)glycine or a salt or an ester thereof.

The process wherein the (phosphonomethyl)amine N-oxide compound is reacted to produce N-(phosphonomethyl)glycine or an ester or a salt thereof through the intermediacy of a condensed alcohol intermediate (formula (IX)) is presented generically in FIG. 2. $R^1$, $R^2$, $R^3$, $R^4$, $R^5$, and $R^{10}$ of FIG. 2 each has the meaning defined previously in this disclosure.

Figure 3:
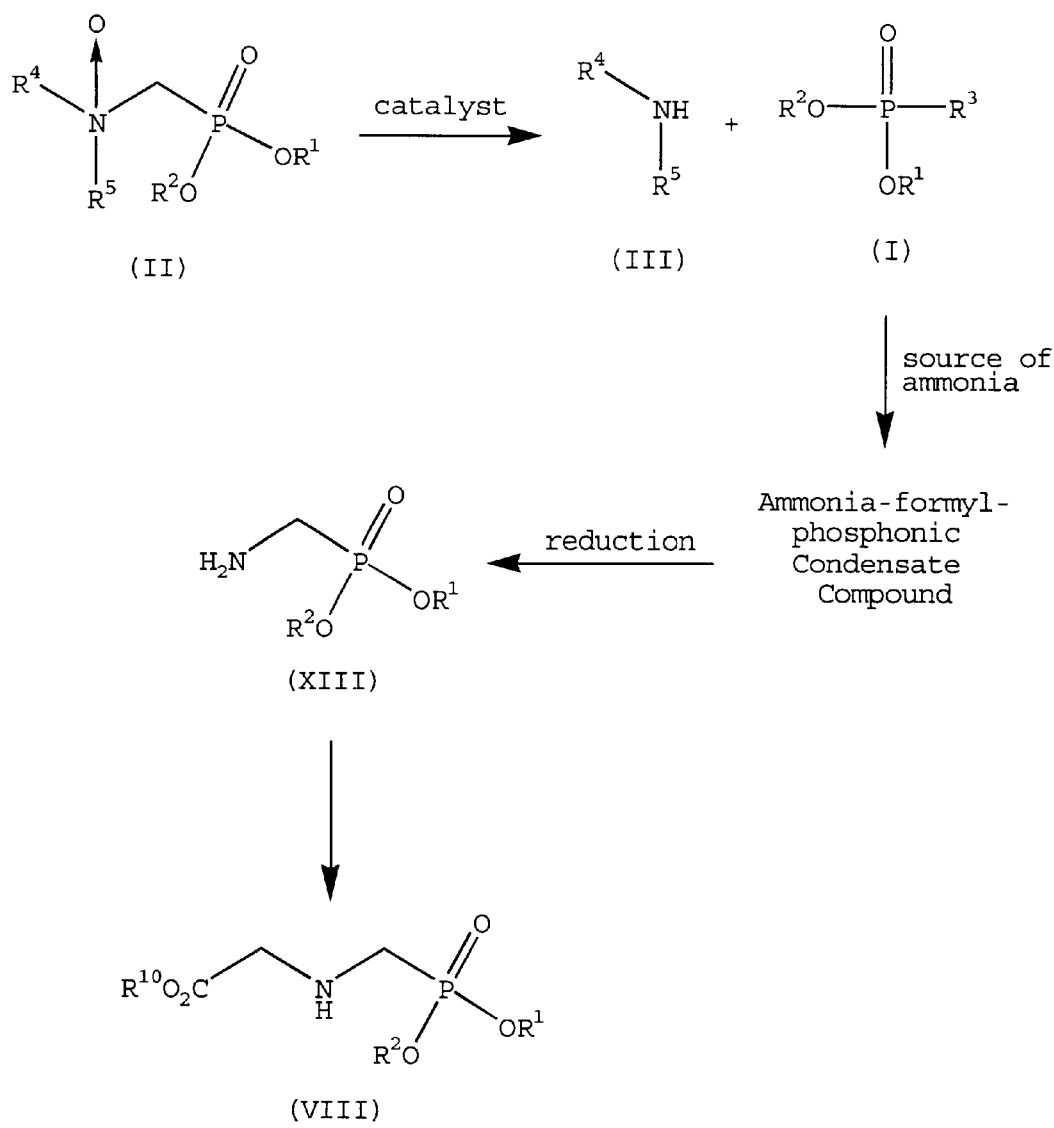
FIG. 3 is a general scheme for the decomposition of a (phosphonomethyl)amine oxide to form a formylphosphonic acid derivative and a dephosphonomethylated amine; the condensation of the formylphosphonic acid derivative with a source of ammonia to form an ammonia-formylphosphonic condensate compound; the reduction of the ammonia-formylphosphonic condensate compound to produce an aminomethylphosphonic acid compound; and the reaction of the aminomethylphosphonic acid compound to produce N-(phosphonomethyl)glycine or a salt or an ester thereof.

It is still another object of the present invention to provide a process for the preparation of N-(phosphonomethyl) glycine, or a salt or an ester thereof wherein the process comprises reacting a (phosphonomethyl)amine N-oxide compound (formula (II)) in the presence of a decomposition catalyst to produce a formylphosphonic acid derivative (formula (III)) and a dephosphonomethylated amine (formula (I)); condensing the formylphosphonic acid derivative with a source of ammonia to form an ammoniaformylphosphonic compound ("AF compound"); reducing the AF compound to form an aminomethylphosphonic acid compound (formula (XIII)) or a zwitterion thereof; and reacting the aminomethylphosphonic acid compound to produce N-(phosphonomethyl)glycine, or a salt or an ester thereof (formula (VIII). Sources of ammonia which are useful in the present invention include ammonia gas, aqueous ammonium hydroxide, urea, and ammonium salts such as ammonium chloride. Franz, et al. (1997), pp. 254–257, herein incorporated by reference, provide several examples by which aminomethylphosphonic acid compounds are reacted to produce N-(phosphonomethyl)glycine. However, given the present disclosure, one of skill in the art will appreciate that numerous other methods for the reaction of aminomethylphosphonic acid compounds to produce N-(phosphonomethyl)glycine can be employed and are contemplated within the scope of the present invention. This overall process is presented generically in FIG. 3 wherein $R^1$ and $R^2$ each has the meaning defined previously in this disclosure. Methods described in U.S. Pat. No. 4,568,432, herein incorporated by reference, for the condensation of glycine with formylphosphonic acid and reduction of the condensed intermediate to form N-(phosphonomethyl) glycine can readily be adapted by one of skill in the art without undue experimentation to perform the condensation of a source of ammonia with formylphosphonic acid and subsequent reduction of the resulting AF compound to produce aminomethylphosphonic acid. An example of a way in which the reduction of the AF compound can be achieved is by hydrogenation. For example, the AF compound can be hydrogenated in the presence of hydrogen and a hydrogenation catalyst such as a noble metal. Examples of noble metals useful as hydrogenation catalysts include platinum, palladium, nickel, and copper. If desired, the catalyst can have a very high surface area, such as Raney nickel. Alternatively, the hydrogenation catalyst can be a supported catalyst such as noble metal on carbon. A useful supported catalyst is palladium on carbon.

A significant advantage of the instant invention over previous reports of the preparation of formylphosphonic acid from tertiary amines is the increased selectivity for the formylphosphonic acid product under the present reaction conditions, relative to reaction conditions in the art. Under the electrochemical conditions taught by Wagenknecht (Synth. React. Inorg. Met.-Org. 12:1–9 (1982)), reported degradation products include phosphoric acid, aminomethylphosphonic acid, and formic acid. Hershman, et al. (U.S. Pat. No. 4,072,706) disclosed that under their reaction conditions formylphosphonic acid degrades to formic acid and phosphorous acid. Because of the degradation of formylphosphonic acid, the processes of the prior disclosures show poor selectivities for formylphosphonic acid. Without limitation, it is believed that the increased selectivity of the present inventive reaction conditions for formylphosphonic acid is due in part to the very short reaction times, e.g. minutes, and mild conditions which the present invention allows. Although at high temperatures and long reaction times the present inventive reaction conditions can lead to some hydrolysis of formylphosphonic acid, the overall mild conditions generally allow minimal hydrolysis. Whatever the precise mechanism, the present invention shows high selectivity for formylphosphonic acid as demonstrated by the examples accompanying this disclosure.

c. Detailed Preparative Methods

The starting materials for use in the methods of preparation of the invention are known or can be prepared by conventional methods known to a skilled person or in an analogous manner to processes described in the art.

Generally, the process methods of the present invention can be performed as follows.

EXAMPLE 1

A 31.4 wt % solution of hydrogen peroxide (1.94 g, 17.9 mmol) was added to nitrilotris(methylenephosphonic acid) (5.00 g, 16.7 mmol) in a 100 mL round bottom flask. A freshly prepared 1.7 wt % solution of $Na_2WO_4$ (0.25 g, 0.013 mmol) was then added and the mixture was magnetically stirred under a nitrogen atmosphere while heating at 85° C. for 2 hours. The resulting nitrilotris (methylenephosphonic acid) N-oxide (NMAO) solution was diluted with deionized water (63 g) and aqueous $VOSO_4$ was added (3.62 wt %, 0.30 g, 0.067 mmol). The mixture was then heated to 75° C for 30 minutes under nitrogen. Analysis of the product mixture by $^{31}P$ NMR revealed complete conversion of NMAO with a selectivity toward FPA of 88%. The dephosphonomethylated amine co-product was the expected iminobis(methylenephosphonic acid) with minor amounts of N-formyl-iminobis (methylenephosphonic acid), nitrilotris(methylenephosphonic acid) and $H_3PO_4$ noted.

EXAMPLE 2

A 31.4% solution of the potassium salt of nitrilotris (methylenephosphonic acid) N-oxide (1.01 g, 0.60 mmol) was acidified with 37% HCl (1.54 g, 15.6 mmol). The acid solution was diluted with 1.95 g of $D_2O$. Analysis by $^{31}P$ NMR showed a large signal corresponding to nitrilotris (methylenephosphonic acid) N-oxide (NMAO) at about 6.3 ppm along with other phosphorus-containing compounds that were impurities in the original commercial solution. Heating the NMR sample at 75° C for 3 hrs led to some minor decomposition of the NMAO to iminobis(methylenephosphonic acid), nitrilotris(methylenephosphonic acid) and $H_3PO_4$. However, addition of 10 microliters of a 0.23 M $VOSO_4$ solution followed by heating to 75° C. for 30 minutes effected complete conversion of the remaining NMAO to formylphosphonic acid and iminobis (methylenephosphonic acid) with a selectivity of about 93%, based on $^{31}P$ NMR analysis.

EXAMPLE 3

Aqueous hydrogen peroxide (30 wt %, 1.99 g, 17.6 mmol) was added over about 30 seconds to a solution of nitrilotris (methylenephosphonic acid) (5.00 g, 16.7 mmol), aqueous vanadyl sulfate (0.27 M, 2.60 microliters, 0.07 mmol), and deionized water (19 mL) at 20–25° C. When the reaction was complete, analysis of the product mixture by $^{31}$P NMR revealed 83% conversion of the starting (phosphonomethyl) amine compound with 77% selectivity to formylphosphonic acid.

EXAMPLE 4

Aqueous hydrogen peroxide (31 wt %, 2.30 g, 21.2 mmol) was added in one portion to a mixture of N-isopropyl iminobis(methylenephosphonic acid) (5.00 g, 20.2 mmol) and sodium tungstate dihydrate (0.02 g, 0.06 mmol) in water (14 g) at 25° C. under nitrogen. The peroxide mixture was then heated at 95° C. for 4 hr which, by $^{31}$P NMR, effected 83% conversion of the tertiary amine to the corresponding N-oxide. Aqueous vanadyl sulfate (0.27 M, 300 microliters, 0.08 mmol) was then added to the N-oxide solution at 50° C. Analysis of the resulting mixture after 30 minutes by $^{31}$P NMR revealed about a 46% yield of FPA based on the initial charge of N-isopropyl iminobis(methylenephosphonic acid).

EXAMPLE 5

To a 59% aqueous formylphosphonic acid solution (5.0 g, 0.23 mol) in deionized water (25 mL) was added glycine (1.56 g, 0.021 mol). The pH of the resultant mixture was adjusted to 7.0 by addition of 2.5 N sodium hydroxide. The reaction mixture was then transferred to a 300 mL autoclave, a 10% palladium on carbon catalyst (1.0 g) added, and the reactor was sealed and pressurized with hydrogen to 6.89× 10$^6$ N/m$^2$ gauge. After 60 minutes of reaction at room temperature, 3.2 g of N-(phosphonomethyl)glycine was obtained representing a 91% yield based on glycine.

EXAMPLE 6

A stock solution of nitrilotris(methylenephosphonic acid) N-oxide (NMAO) was prepared by heating a mixture of purified nitrilotris(methylenephosphonic acid) (NMA, 15.00 g, 50.16 mmol), deionized water (15 g), aqueous hydrogen peroxide (31.4 wt %, 5.72 g, 52.8 mmol), and aqueous sodium tungstate (1.7 wt %, 0.74 g, 0.043 mmol) to 85° C. for 2.5 hours under a nitrogen atmosphere. Portions of the resulting solution, estimated to be 43 wt % NMAO, were placed in separate glass vials and diluted with deionized water to provide a range of initial NMAO concentrations ([NMAO]$_i$). Next, an aqueous vanadyl sulfate solution (0.23 M) was added to provide an NMAO/VO$^{2+}$ mole ratio in each vial of 240. The sealed vials were then immersed in a water bath at 65° C. for 30 min. Analysis of each sample was performed by $^{31}$P NMR and selectivities were determined from signal integrations by averaging the results of two methods:

$$\frac{[FPA]}{([FPA]+[H_3PO_3]+[H_3PO_4])} \times 100 = FPA \text{ selectivity "A"}$$

$$\frac{[FPA]}{\left(\frac{[NFI]}{2}+\frac{[IB]}{2}\right)} \times 100 = FPA \text{ selectivity "B"}$$

wherein:
[FPA]=integrated $^{31}$P NMR area for formylphosphonic acid
[H$_3$PO$_3$]=integrated $^{31}$P NMR area for phosphorous acid
[H$_3$PO$_4$]=integrated $^{31}$P NMR area for phosphoric acid
[IB]=integrated $^{31}$P NMR area for iminobis (methylenephosphonic acid), and
[NFI]=integrated $^{31}$P NMR area for N-formyliminobis (methylene-phosphonic acid).

Figure 4:
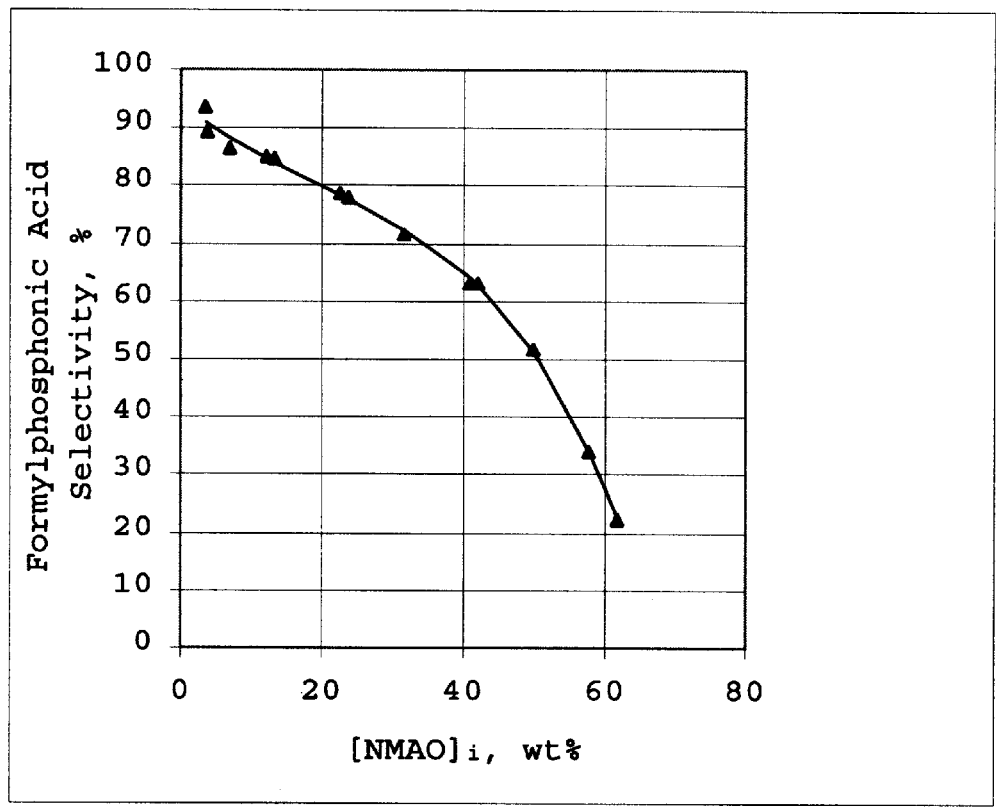
FIG. 4 is a graph of selectivity for formylphosphonic acid in the decomposition reaction of nitrilotris (methylenephosphonic acid) N-oxide.

The effect on selectivity for formylphosphonic acid by various [NMAO]$_i$ is plotted in FIG. 4. The data show that selectivity for formylphosphonic acid increases as [NMAO]$_i$ decreases.

The examples herein can be performed by substituting the generically or specifically described reactants and/or operating conditions of this invention for those used in the preceding examples.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A process for preparing a formylphosphonic acid derivative, said process comprising decomposing a (phosphonomethyl)amine N-oxide compound in the presence of a decomposition catalyst to produce said formylphosphonic acid derivative and a dephosphonomethylated amine.

2. The process of claim 1 wherein said formylphosphonic acid derivative has a structure of formula (I):

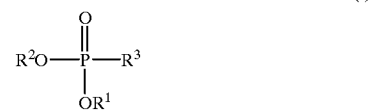

said (phosphonomethyl)amine N-oxide compound has a structure of formula (II):

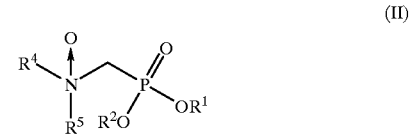

said dephosphonomethylated amine has a structure of formula (III):

and wherein:
R$^1$ and R$^2$ are independently selected from the group consisting of H, hydrocarbyl, substituted hydrocarbyl, heterocycle, and a salt-forming cation, and R$^1$ and R$^2$ taken together with the oxygen and phosphorus atoms to which they are attached optionally form a cyclic structure;
R$^3$ is selected from the group consisting of —CHO and —CH(OR$^8$)(OR$^9$);
R$^4$ and R$^5$ are independently selected from the group consisting of H, —CH$_2$PO(OR$^6$)(OR$^7$), hydrocarbyl, substituted hydrocarbyl, and heterocycle, and R$^4$ and R$^5$ taken together with the nitrogen atom to which they are attached optionally form a cyclic structure;
R$^6$ and R$^7$ are independently selected from the group consisting of H, hydrocarbyl, substituted hydrocarbyl, heterocycle, and a salt-forming cation, and $R^6$ and $R^7$ taken together with the oxygen and phosphorus atoms to which they are attached optionally form a cyclic structure; and $R^8$ and $R^9$ are independently selected from the group consisting of H, hydrocarbyl, substituted hydrocarbyl, and heterocycle, and $R^8$ and $R^9$ taken together with the oxygen and carbon atoms to which they are attached optionally form a cyclic structure.

3. The process of claim 2 wherein the temperature is in the range of about 0° C. to about 150° C.

4. The process of claim 3 wherein the temperature is in the range of about 20° C. to about 110° C.

5. The process of claim 4 wherein the temperature is in the range of about 20° C. to about 75° C.

6. The process of claim 2 wherein said (phosphonomethyl)amine N-oxide is decomposed under neutral or acidic conditions.

7. The process of claim 6 wherein decomposition of said (phosphonomethyl)amine N-oxide compound is performed at about pH 3 or less.

8. The process of claim 2 further comprising reacting said dephosphonomethylated amine under phosphonomethylation conditions to produce a (phosphonomethyl)amine compound and oxidizing said (phosphonomethyl)amine compound to regenerate said (phosphonomethyl)amine N-oxide compound.

9. The process of claim 8 wherein said phosphonomethylation conditions comprise reacting said dephosphonomethylated amine in the presence of phosphorus trichloride, water, and a source of formaldehyde to produce said (phosphonomethyl)amine compound.

10. The process of claim 8 wherein said phosphonomethylation conditions comprise reacting said dephosphonomethylated amine in the presence of phosphorous acid, a strong mineral acid, and a source of formaldehyde to produce said (phosphonomethyl)amine compound.

11. The process of claim 2 wherein at least one of $R^4$ and $R^5$ is —$CH_2PO(OR^6)(OR^7)$.

12. The process of claim 11 wherein one of $R^4$ and $R^5$ is —$CH_2PO(OR^6)(OR^7)$ and the other of $R^4$ and $R^5$ is 2-hydroxyethyl.

13. The process of claim 2 wherein $R^4$ and $R^5$ are independently selected from the group consisting of —$CH_2PO(OR^6)(OR^7)$ and hydrocarbyl.

14. The process of claim 13 wherein $R^4$ and $R^5$ are both —$CH_2PO(OR^6)(OR^7)$.

15. The process of claim 13 wherein $R^4$ and $R^5$ are both hydrocarbyl.

16. The process of claim 13 wherein one of $R^4$ and $R^5$ is hydrocarbyl and the other of $R^4$ and $R^5$ is —$CH_2PO(OR^6)(OR^7)$.

17. The process of claim 2 wherein the decomposition catalyst comprises a metal.

18. The process of claim 17 wherein the decomposition catalyst comprises a metal selected from the group consisting of iron, zinc, aluminum, vanadium, molybdenum, and copper.

19. The process of claim 18 wherein the metal is in a zero valence state.

20. The process of claim 18 wherein the metal is in a metallic form.

21. The process of claim 18 wherein the metal is in a salt or an oxide form.

22. The process of claim 18 wherein the decomposition catalyst comprises a compound selected from the group consisting of a vanadium salt, an iron salt, and a copper salt.

23. The process of claim 18 wherein the decomposition catalyst comprises a compound selected from the group consisting of vanadium pentoxide, vanadyl sulfate, vanadium chloride, ferrous sulfate, ferrous chloride, and ferrous bromide.

24. The process of claim 23 wherein the decomposition catalyst comprises a compound selected from the group consisting of vanadium pentoxide, vanadyl sulfate, and vanadium chloride.

25. The process of claim 24 wherein the decomposition catalyst comprises vanadyl sulfate.

26. The process of claim 18 wherein the decomposition catalyst comprises a water-soluble decomposition catalyst.

27. The process of claim 2 conducted in a continuous reaction zone into which said (phosphonomethyl)amine N-oxide compound is continuously or intermittently introduced and from which a reaction product mixture comprising said formylphosphonic acid derivative is continuously or intermittently withdrawn.

28. The process of claim 2 wherein said (phosphonomethyl)amine N-oxide compound is prepared by oxidizing a (phosphonomethyl)amine compound with a peroxide in the presence of an oxidation catalyst to produce said (phosphonomethyl)amine N-oxide.

29. The process of claim 28 wherein said (phosphonomethyl)amine compound is nitrilotris(methylenephosphonic acid).

30. The process of claim 28 wherein said peroxide is selected from the group consisting of hydrogen peroxide, performic acid, peracetic acid, perbenzoic acid, peroxytrifluoroacetic acid, benzoyl peroxide, benzenepersulfonic acid, and combinations thereof.

31. The process of claim 30 wherein said peroxide comprises hydrogen peroxide.

32. The process of claim 28 wherein said oxidation catalyst comprises a metal.

33. The process of claim 32 wherein said oxidation catalyst comprises a transition metal.

34. The process of claim 33 wherein said oxidation catalyst comprises a transition metal selected from the group consisting of molybdenum, tungsten, cobalt, silver, iron, nickel, chromium, ruthenium, vanadium, cerium, manganese, and salts and complexes thereof.

35. The process of claim 34 wherein said oxidation catalyst comprises a transition metal selected from the group consisting of tungsten, cobalt, vanadium, cerium, manganese, and salts and complexes thereof.

36. The process of claim 35 wherein said oxidation catalyst comprises a transition metal selected from the group consisting of tungsten, cobalt, vanadium, and salts and complexes thereof.

37. The process of claim 36 wherein said oxidation catalyst comprises tungsten or a salt or complex thereof.

38. The process of claim 37 wherein said oxidation catalyst comprises sodium tungstate.

39. The process of claim 34 wherein said oxidation catalyst comprises molybdenum.

40. The process of claim 39 wherein the reaction mixture further comprises a metabisulfite compound.

41. The process of claim 40 wherein said metabisulfite compound comprises sodium metabisulfite.

42. The process of claim 32 wherein said oxidation catalyst comprises a metal selected from the group consisting of aluminum, tin, lead, and salts and complexes thereof.

43. The process of claim 2 wherein the decomposition is performed in the presence of a solvent.

44. The process of claim 43 wherein said solvent comprises a material selected from the group consisting of water and an organic solvent.

45. The process of claim 44 wherein said solvent comprises an organic solvent.

46. The process of claim 45 wherein said organic solvent comprises an alcohol.

47. The process of claim 46 wherein said alcohol is selected from the group consisting of aliphatic alcohols, aromatic alcohols, glycols, polyols, and unsaturated alcohols.

48. The process of claim 44 wherein said solvent comprises water.

49. The process of claim 28 wherein the oxidation of said (phosphonomethyl)amine compound to said (phosphonomethyl)amine N-oxide compound and the decomposition of said (phosphonomethyl)amine N-oxide compound to said formylphosphonic acid derivative and said dephosphonomethylated amine is performed in a single vessel.

50. The process of claim 49 wherein said oxidation catalyst comprises said decomposition catalyst.

51. The process of claim 50 wherein said oxidation catalyst comprises a compound selected from the group consisting of vanadium metal, a vanadium salt, and an oxide of vanadium.

52. The process of claim 50 wherein said oxidation catalyst comprises vanadyl sulfate.

53. The process of claim 28 wherein the oxidation of said (phosphonomethyl)amine compound to said (phosphonomethyl)amine N-oxide compound and the decomposition of said (phosphonomethyl)amine N-oxide compound to said formylphosphonic acid derivative and said dephosphonomethylated amine are performed in two or more steps.

54. A process for preparing formylphosphonic acid or a salt or a hydrate thereof, said process comprising oxidizing nitrilotris(methylenephosphonic acid) or a salt thereof to form nitrilotris(methylenephosphonic acid) N-oxide or a salt thereof, and decomposing said nitrilotris(methylenephosphonic acid) N-oxide or salt thereof in the presence of a decomposition catalyst to form formylphosphonic acid or a salt thereof.

55. The process of claim 54 wherein the oxidation of nitrilotris(methylenephosphonic acid) comprises contacting nitrilotris(methylenephosphonic acid) with a peroxide in the presence of an oxidation catalyst.

56. The process of claim 55 wherein said peroxide comprises hydrogen peroxide.

57. The process of claim 55 wherein said oxidation catalyst comprises a metal.

58. The process of claim 57 wherein said oxidation catalyst comprises a transition metal.

59. The process of claim 58 wherein said oxidation catalyst comprises a transition metal selected from the group consisting of molybdenum, tungsten, cobalt, silver, iron, nickel, chromium, ruthenium, vanadium, cerium, manganese, and salts and complexes thereof.

60. The process of claim 59 wherein said oxidation catalyst comprises a transition metal selected from the group consisting of tungsten, cobalt, vanadium, cerium, manganese, and salts and complexes thereof.

61. The process of claim 60 wherein said oxidation catalyst comprises a transition metal selected from the group consisting of tungsten, cobalt, vanadium, and salts and complexes thereof.

62. The process of claim 61 wherein said oxidation catalyst comprises tungsten or a salt or complex thereof.

63. The process of claim 62 wherein said oxidation catalyst comprises sodium tungstate.

64. The process of claim 59 wherein said oxidation catalyst comprises molybdenum.

65. The process of claim 64 wherein the reaction mixture further comprises a metabisulfite compound.

66. The process of claim 65 wherein said metabisulfite compound comprises sodium metabisulfite.

67. The process of claim 57 wherein said oxidation catalyst comprises a metal selected from the group consisting of aluminum, tin, lead, and salts and complexes thereof.

68. The process of claim 54 wherein said decomposition catalyst comprises a metal.

69. The process of claim 68 wherein said decomposition catalyst comprises a metal selected from the group consisting of iron, zinc, aluminum, vanadium, molybdenum, and copper.

70. The process of claim 69 wherein the metal is in a zero valence state.

71. The process of claim 70 wherein the metal is in a metallic form.

72. The process of claim 69 wherein the metal is in a salt or an oxide form.

73. The process of claim 72 wherein the decomposition catalyst comprises a compound selected from the group consisting of a vanadium salt, an iron salt, and a copper salt.

74. The process of claim 69 wherein the decomposition catalyst comprises a compound selected from the group consisting of vanadium pentoxide, vanadyl sulfate, vanadium chloride, ferrous sulfate, ferrous chloride, and ferrous bromide.

75. The process of claim 74 wherein said decomposition catalyst comprises a compound selected from the group consisting of vanadium pentoxide, vanadyl sulfate, and vanadium chloride.

76. The process of claim 75 wherein said decomposition catalyst comprises vanadyl sulfate.

77. The process of claim 69 wherein said decomposition catalyst comprises a water-soluble decomposition catalyst.

78. The process of claim 54 wherein said decomposition is performed at a temperature in the range of about 0° C. to about 150° C.

79. The process of claim 78 wherein said decomposition is performed at a temperature in the range of about 20° C. to about 110° C.

80. The process of claim 79 wherein said decomposition is performed at a temperature in the range of about 20° C. to about 75° C.

81. The process of claim 54 wherein said (phosphonomethyl)amine N-oxide is decomposed under neutral or acidic conditions.

82. The process of claim 81 wherein decomposition of said (phosphonomethyl)amine N-oxide is performed at about pH 3 or less.

83. The process of claim 54 wherein said decomposition is performed in the presence of a solvent.

84. The process of claim 83 wherein said solvent comprises a material selected from the group consisting of water and an organic solvent.

85. The process of claim 84 wherein said solvent comprises an organic solvent.

86. The process of claim 85 wherein said organic solvent comprises an alcohol.

87. The process of claim 86 wherein said alcohol is selected from the group consisting of aliphatic alcohols, aromatic alcohols, glycols, polyols, and unsaturated alcohols.

88. The process of claim 84 wherein said solvent comprises water.

89. The process of claim 54 wherein the oxidation of said (phosphonomethyl)amine compound to said (phosphonomethyl)amine N-oxide compound and the decomposition of said (phosphonomethyl)amine N-oxide compound to said formylphosphonic acid derivative and said dephosphonomethylated amine are performed in a single vessel.

90. The process of claim 89 wherein said oxidation catalyst comprises said decomposition catalyst.

91. The process of claim 90 wherein said oxidation catalyst comprises a compound selected from the group consisting of vanadium, a vanadium salt, and a vanadium oxide.

92. The process of claim 90 wherein said oxidation catalyst comprises vanadyl sulfate.

93. The process of claim 54 wherein the oxidation of said (phosphonomethyl)amine compound to said (phosphonomethyl)amine N-oxide compound and the decomposition of said (phosphonomethyl)amine N-oxide compound to said formylphosphonic acid derivative and said dephosphonomethylated amine are performed in two or more steps.

94. A process for preparing N-(phosphonomethyl)glycine, or a salt or an ester thereof, wherein said process comprises decomposing a (phosphonomethyl)amine N-oxide compound in the presence of a decomposition catalyst to produce a formylphosphonic acid derivative and a dephosphonomethylated amine, and reacting said formylphosphonic acid derivative to produce N-(phosphonomethyl)glycine, or a salt or an ester thereof, wherein:

said formylphosphonic acid derivative has a structure of formula (I):

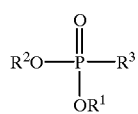

(I)

said (phosphonomethyl)amine N-oxide compound has a structure of formula (II):

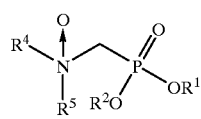

(II)

said dephosphonomethylated amine has a structure of formula (III):

(III)

and wherein:
$R^1$ and $R^2$ are independently selected from the group consisting of H, hydrocarbyl, substituted hydrocarbyl, heterocycle, and a salt-forming cation, and $R^1$ and $R^2$ taken together with the oxygen and phosphorus atoms to which they are attached optionally form a cyclic structure;
$R^3$ is selected from the group consisting of —CHO and —CH($OR^8$)($OR^9$);

$R^4$ and $R^5$ are independently selected from the group consisting of H, —$CH_2PO(OR^6)(OR^7)$, hydrocarbyl, substituted hydrocarbyl, and heterocycle, and $R^4$ and $R^5$ taken together with the nitrogen atom to which they are attached optionally form a cyclic structure;

$R^6$ and $R^7$ are independently selected from the group consisting of H, hydrocarbyl, substituted hydrocarbyl, heterocycle, and a salt-forming cation, and $R^6$ and $R^7$ taken together with the oxygen and phosphorus atoms to which they are attached optionally form a cyclic structure; and $R^8$ and $R^9$ are independently selected from the group consisting of H, hydrocarbyl, substituted hydrocarbyl, and heterocycle, and $R^8$ and $R^9$ taken together with the oxygen and carbon atoms to which they are attached optionally form a cyclic structure.

95. The process of claim 94 wherein the reaction of said formylphosphonic acid derivative to produce N-(phosphonomethyl)glycine comprises condensing said formylphosphonic acid derivative with a glycine compound having a structure of formula (XI)

(XI)

or a zwitterion thereof to form a condensed carboxylate intermediate, and reducing said condensed carboxylate intermediate to produce N-(phosphonomethyl)glycine or a salt or an ester thereof, wherein $R^{10}$ is selected from the group consisting of H, hydrocarbyl, substituted hydrocarbyl, heteroaryl, and a salt-forming cation.

96. The process of claim 95 wherein the reduction of said condensed carboxylate intermediate comprises reacting said condensed carboxylate intermediate in the presence of hydrogen and a hydrogenation catalyst.

97. The process of claim 96 wherein said hydrogenation catalyst comprises a noble metal.

98. The process of claim 97 wherein said hydrogenation catalyst comprises a noble metal selected from the group consisting of platinum, palladium, nickel, and copper.

99. The process of claim 98 wherein said hydrogenation catalyst comprises Raney nickel.

100. The process of claim 98 wherein said hydrogenation catalyst further comprises a solid support.

101. The process of claim 100 wherein said solid support comprises a carbon solid support.

102. The process of claim 101 wherein said hydrogenation catalyst comprises palladium on carbon.

103. The process of claim 94 wherein the reaction of said formylphosphonic acid derivative to produce N-(phosphonomethyl)glycine comprises condensing said formylphosphonic acid derivative with 1-amino-2-hydroxyethane to form a condensed alcohol intermediate, reducing said condensed alcohol intermediate to produce an N-(2-hydroxyethyl)-N-(phosphonomethyl)amine compound having a structure of formula (X)

(X)

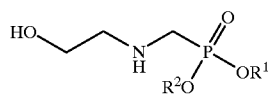

or a zwitterion thereof, and oxidizing said N-(2-hydroxyethyl)-N-(phosphonomethyl)amine compound to produce N-(phosphonomethyl)glycine or a salt or an ester thereof, wherein:

$R^1$ and $R^2$ are independently selected from the group consisting of H, hydrocarbyl, substituted hydrocarbyl, heterocycle, and a salt-forming cation, and $R^1$ and $R^2$ taken together with the oxygen and phosphorus atoms to which they are attached optionally form a cyclic structure; and $R^{10}$ is selected from the group consisting of is selected from the group consisting of H, hydrocarbyl, substituted hydrocarbyl, heteroaryl, and a salt-forming cation.

104. The process of claim 103 wherein the reduction of said condensed alcohol intermediate comprises reacting said condensed alcohol intermediate in the presence of hydrogen and a hydrogenation catalyst.

105. The process of claim 104 wherein said hydrogenation catalyst comprises a noble metal.

106. The process of claim 105 wherein said hydrogenation catalyst comprises a noble metal selected from the group consisting of platinum, palladium, nickel, and copper.

107. The process of claim 106 wherein said hydrogenation catalyst comprises Raney nickel.

108. The process of claim 106 wherein said hydrogenation catalyst further comprises a solid support.

109. The process of claim 108 wherein said solid support comprises a carbon solid support.

110. The process of claim 109 wherein said hydrogenation catalyst comprises palladium on carbon.

111. The process of claim 103 wherein the oxidation of said N-(2-hydroxyethyl)-N-(phosphonomethyl)amine compound comprises dehydrogenation.

112. The process of claim 94 wherein the formylphosphonic acid derivative is condensed with a source of ammonia to form an ammonia-formylphosphonic condensate compound, reducing the ammonia-formylphosphonic condensate compound to form an aminomethylphosphonic acid compound having a structure of formula (XIII)

(XIII)

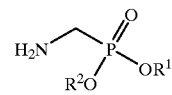

or a zwitterion thereof, and reacting the aminomethylphosphonic acid compound to produce N-(phosphonomethyl)glycine or a salt or an ester thereof, wherein $R^1$ and $R^2$ are independently selected from the group consisting of H, hydrocarbyl, substituted hydrocarbyl, heterocycle, and a salt-forming cation, and $R^1$ and $R^2$ taken together with the oxygen and phosphorus atoms to which they are attached optionally form a cyclic structure.

113. The process of claim 112 wherein the reduction of said ammonia-formylphosphonic condensate compound comprises reacting said ammonia-formylphosphonic condensate compound in the presence of hydrogen and a hydrogenation catalyst.

114. The process of claim 113 wherein said hydrogenation catalyst comprises a noble metal.

115. The process of claim 114 wherein said hydrogenation catalyst comprises a noble metal selected from the group consisting of platinum, palladium, nickel, and copper.

116. The process of claim 115 wherein said hydrogenation catalyst comprises Raney nickel.

117. The process of claim 115 wherein said hydrogenation catalyst further comprises a solid support.

118. The process of claim 117 wherein said solid support comprises a carbon solid support.

119. The process of claim 118 wherein said hydrogenation catalyst comprises palladium on carbon.

120. The process of claim 112 wherein the oxidation of said N-(2-hydroxyethyl)-N-(phosphonomethyl)amine compound comprises dehydrogenation.

\* \* \* \* \*

UNITED STATES PATENT AND TRADEMARK OFFICE
CERTIFICATE OF CORRECTION

PATENT NO. : 6,274,760 B1
DATED : August 14, 2001
INVENTOR(S) : Thaddeus S. Franczyk, II It is certified that error appears in the above-identified patent and that said Letters Patent is hereby corrected as shown below:

<u>Column 15, claim 12,</u>
Line 41, insert -- $^6$ -- after the first occurrence of "R"

Signed and Sealed this

Nineteenth Day of March, 2002

Attest:

JAMES E. ROGAN
*Director of the United States Patent and Trademark Office*

*Attesting Officer*